US008980642B2

(12) United States Patent
Karas et al.

(10) Patent No.: US 8,980,642 B2
(45) Date of Patent: Mar. 17, 2015

(54) USE OF CYANOCINNAMIC ACID DERIVATIVES AS MATRICS IN MALDI MASS SPECTROMETRY

(75) Inventors: Michael Karas, Hattersheim (DE); Thorsten Wolfgang Jaskolla, Weiterstadt (DE)

(73) Assignee: Sigma-Aldrich International GmbH, St. Gallen (CH)

( * ) Notice: Subject to any disclaimer, the term of this patent is extended or adjusted under 35 U.S.C. 154(b) by 1176 days.

(21) Appl. No.: 12/675,569

(22) PCT Filed: Jul. 10, 2008

(86) PCT No.: PCT/DE2008/001149
§ 371 (c)(1),
(2), (4) Date: Feb. 1, 2011

(87) PCT Pub. No.: WO2009/026867
PCT Pub. Date: Mar. 5, 2009

(65) Prior Publication Data
US 2011/0121166 A1 May 26, 2011

(30) Foreign Application Priority Data
Aug. 27, 2007 (DE) .......................... 10 2007 040 251

(51) Int. Cl.
*G01N 24/00* (2006.01)
*G01N 33/68* (2006.01)
(52) U.S. Cl.
CPC .................................. *G01N 33/6851* (2013.01)
USPC ........................................... 436/173; 326/86
(58) Field of Classification Search
CPC ............ G01N 33/6851; G01N 33/6848; H01J 49/0418; H01J 49/164

USPC .................................................... 436/173, 86
See application file for complete search history.

(56) References Cited

U.S. PATENT DOCUMENTS

| | | | |
|---|---|---|---|
| 2002/0142982 A1 | 10/2002 | Hla et al. | |
| 2006/0040334 A1 | 2/2006 | Thompson | |
| 2006/0246225 A1 | 11/2006 | Moritz et al. | |

FOREIGN PATENT DOCUMENTS

| | | |
|---|---|---|
| DE | 101 58 860 | 6/2003 |
| DE | 103 22 701 | 12/2004 |
| WO | WO 2006/124003 | 11/2006 |

OTHER PUBLICATIONS

Cohen and Chait, "Influence of Matrix Solution Conditions on the MALDI-MS Analysis of Peptides and Proteins", Anal. Chem., 1996, vol. 68, No. 1, pp. 31-37.*
Towers et al. "Introduction of 4-Chloro-r-cyanocinnamic Acid Liquid Matrices for High Sensitivity UV-MALDI MS", Journal of Proteome Research 2010, v. 9, pp. 1931-1940.*
Beavis and Chait. "Cinnamic Acid Derivaties as Matrices for Ultraviolet Laser Desporption Mass Spectrometry of Proteins." *Rapid Communications in Mass Spectrometry*. vol. 3. No. 12. 1989. pp. 432-435.
Tholey et al. "Ionic (liquid) matrices for matrix-assisted laser desorption/ionization mass spectrometry-applications and perspectives." *Anal Bioanal Chem*. vol. 386. 2006. pp. 24-37.
Jaskolla et al. "4-Chloro-α-cyanocinnamic acid is an advanced, rationally designed MALDI matrix." *PNAS*. vol. 105. No. 34. pp. 12200-12205, 2008.

* cited by examiner

*Primary Examiner* — Yelena G Gakh
(74) *Attorney, Agent, or Firm* — Arthur M. Reginelli; Renner, Kenner

(57) ABSTRACT

The present invention relates to the use of cyanocinnamic acid derivatives as a matrix in the MALDI mass spectrometry of an analyte.

10 Claims, 8 Drawing Sheets

USE OF CYANOCINNAMIC ACID DERIVATIVES AS MATRICES IN MALDI MASS SPECTROMETRY

Figure 1:
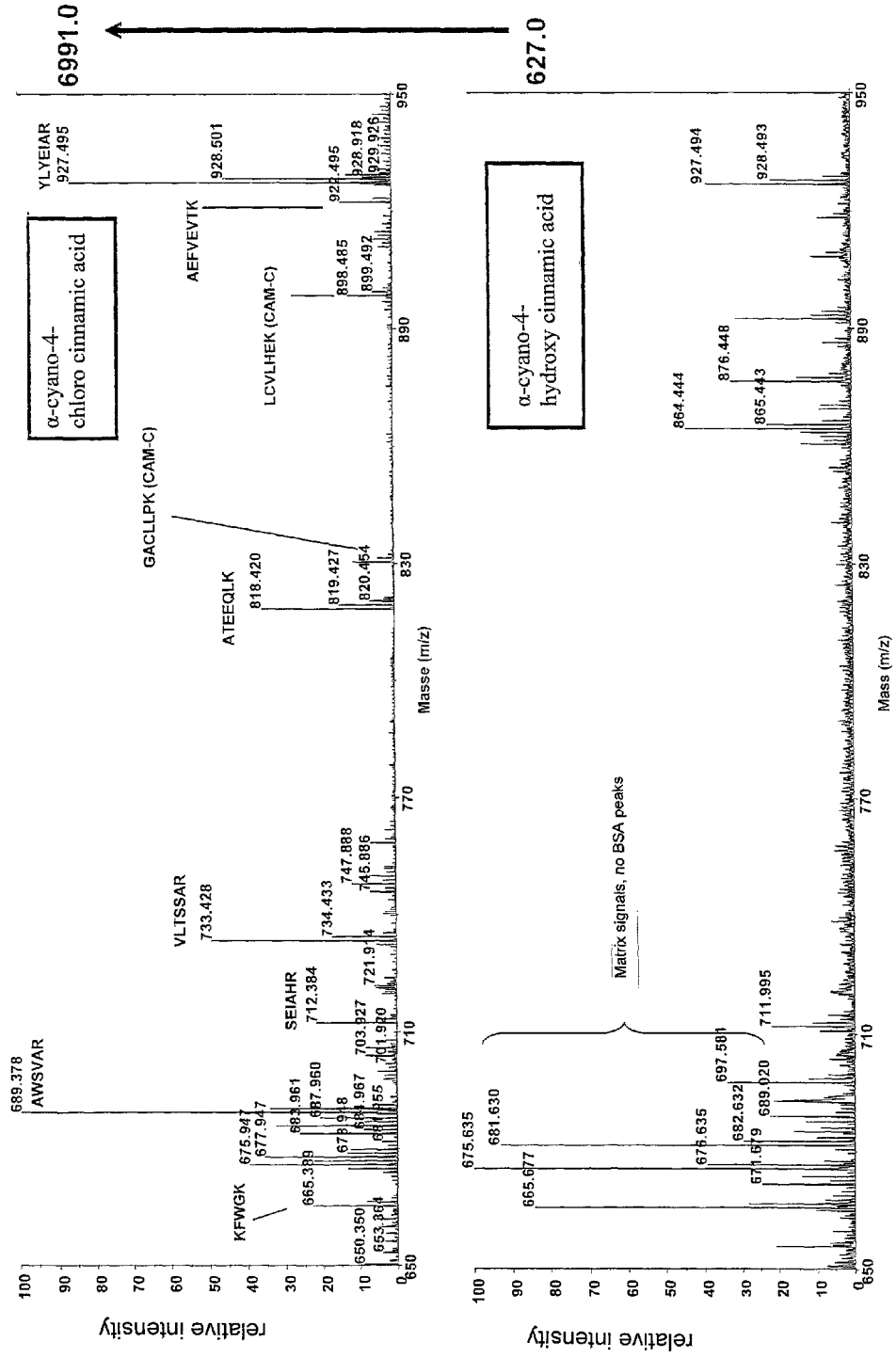
Figure 2:
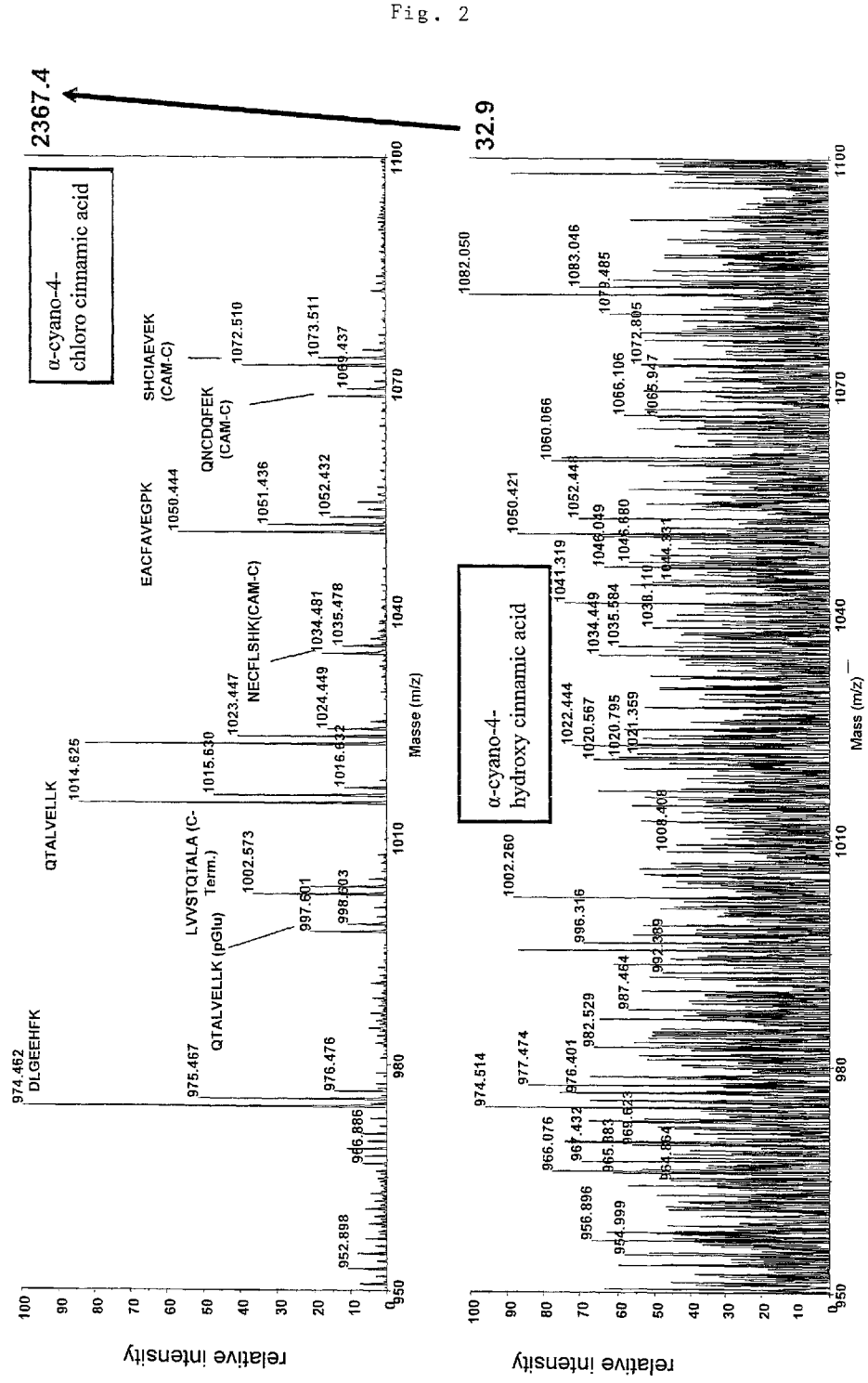
Figure 3:
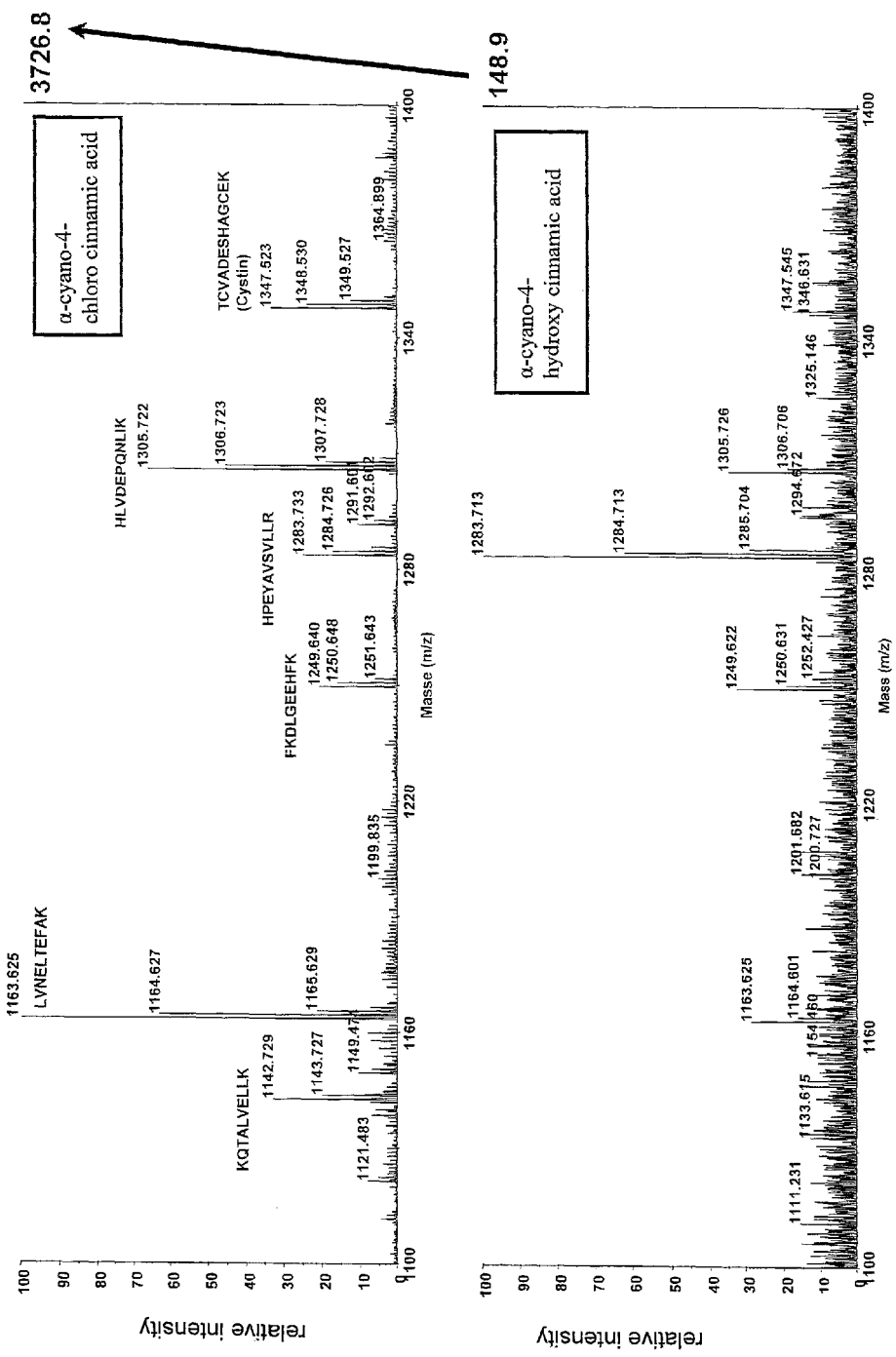
Figure 4:
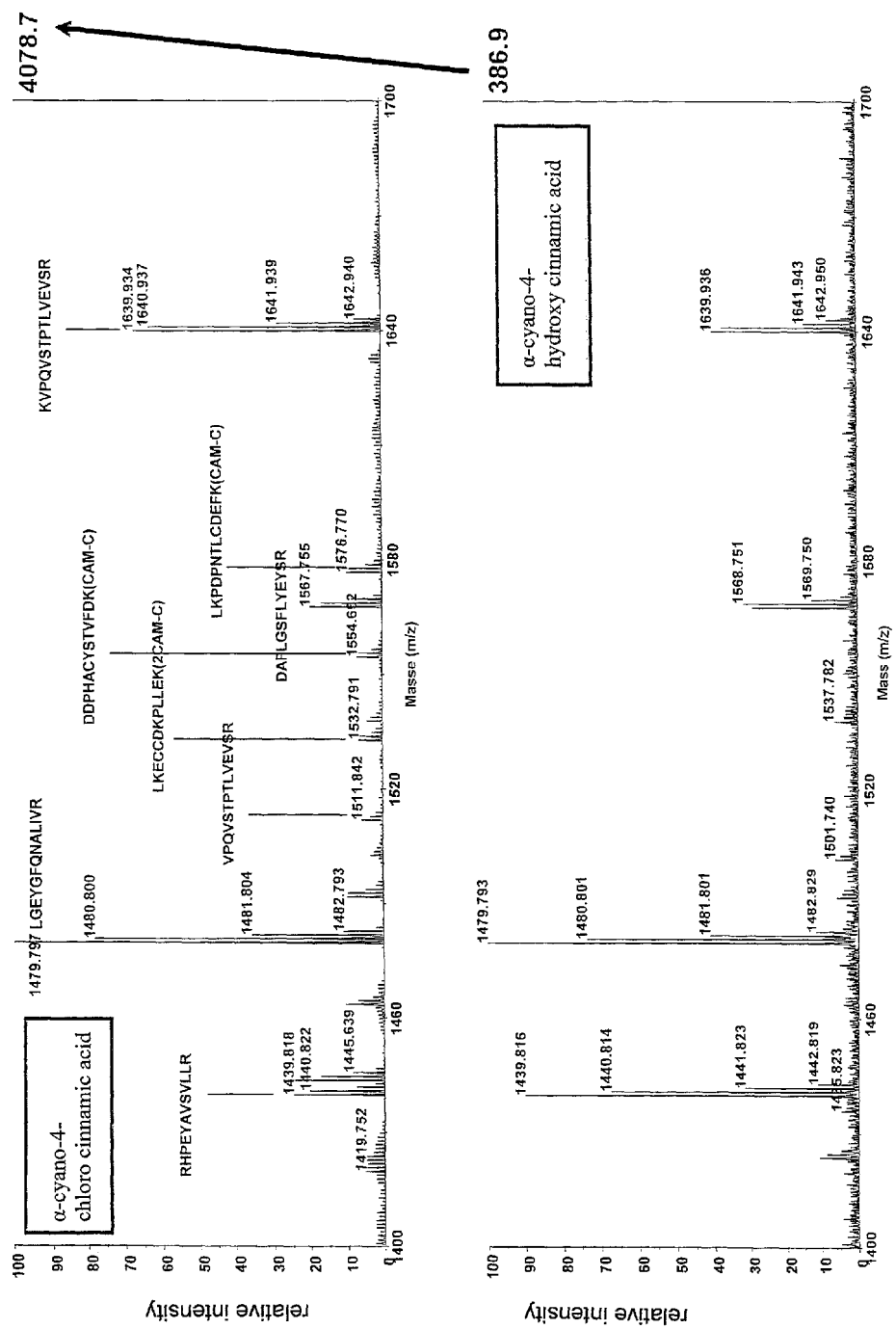
Figure 5:
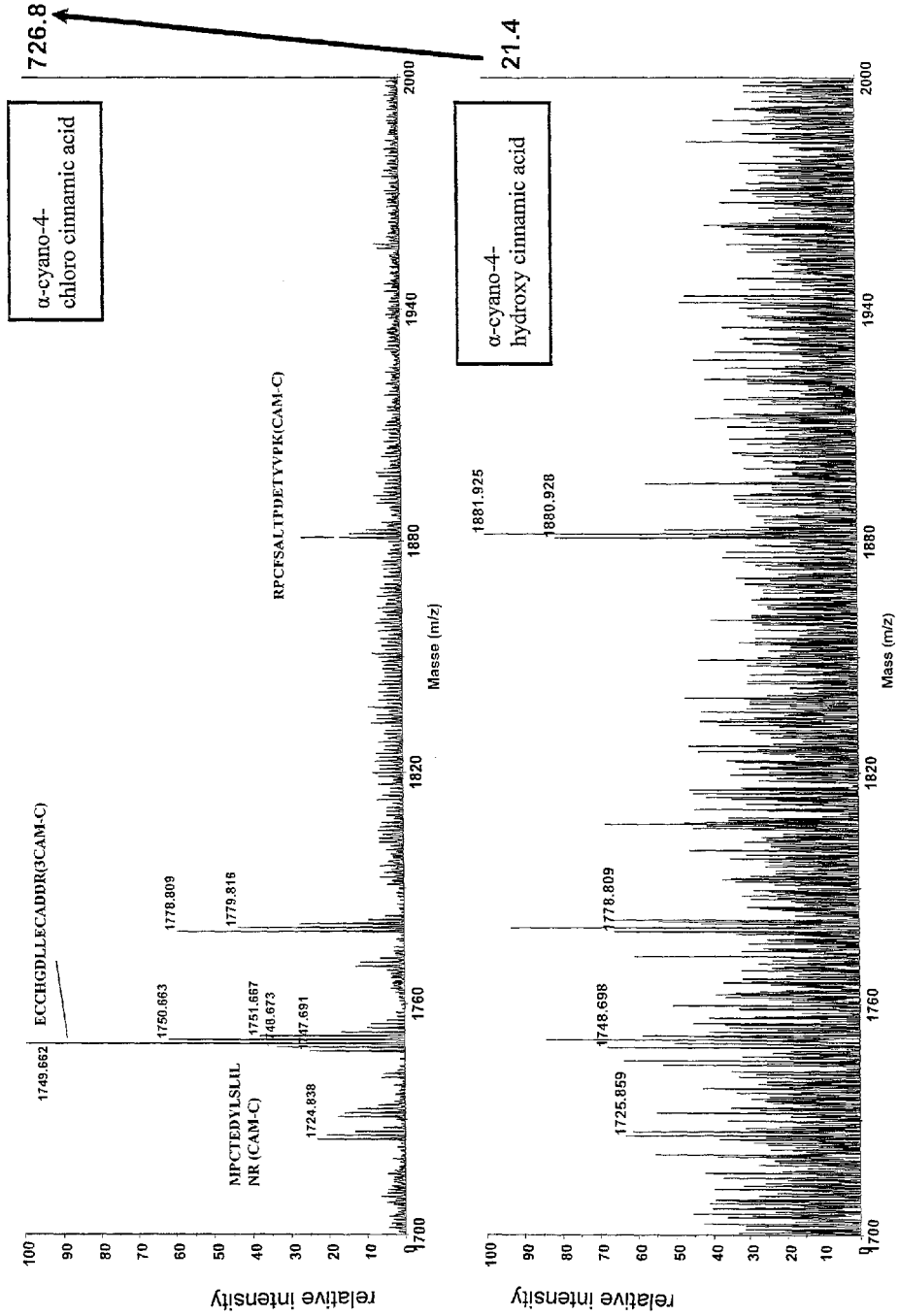

This application is a National Stage Application of PCT/DE2008/001149, filed 10 Jul. 2008, which claims benefit of Serial No. 10 2007 040 251.3, filed 27 Aug. 2007 in Germany and which applications are incorporated herein by reference. To the extent appropriate, a claim of priority is made to each of the above disclosed applications.

The present invention relates to the use of cyanocinnamic acid derivatives as a matrix in MALDI mass spectrometry of analytes.

MALDI (Matrix Assisted Laser Desorption/Ionisation) is a process for the ionisation of molecules. Since its development in the 1980s, it has proven particularly effective for the mass spectrometry of large molecules and polymers and also biopolymers. MALDI is based on the co-crystallisation of a matrix and an analyte with a distinct molar excess of matrix. Matrix substances chosen are small organic molecules which absorb energy at the laser wavelengths used. The matrix makes it easier to generate intact gas phase ions on a large scale from large, non-volatile and thermally unstable compounds, such as peptides, proteins, oligonucleotides, synthetic polymers and large inorganic compounds. The matrices can be used for virtually all substances suitable for analysing with MALDI-MS, i.e. for large and small, non-volatile and thermally unstable compounds, such as biological macromolecules, e.g. proteins and lipids, and small, organic and inorganic analytes, such as medicinal substances, plant metabolites and the like. The main field of use is the analysis of peptides. A laser beam (UV or IR-pulsed laser) is used as the source of energy for desorption and ionisation.

The matrix plays a key role in that it absorbs the laser light energy and in an excited state ablates a small part of the matrix-analyte co-crystals, as a result of which probe molecules enter the gas phase. As a result of the interaction between the matrix and the analyte, analyte ions arise which, after their formation, are transferred electrostatically to a mass spectrometer, in which they are separated from the matrix ions and can be detected individually.

Thus far, small organic molecules have been used as matrix substances, such as compounds with unstable protons, such as carboxylic acids. The best-known matrix compound is the most commonly used α-cyano-4-hydroxy cinnamic acid (CHCA or HCCA). Examples of other matrices used in MALDI-MS are sinapic acid (4-hydroxy-3,5-dimethoxy cinnamic acid) or 2,5-dihydroxy benzoic acid (2,5-DHB).

Beavis, R. C.; Chait, B. T.: Cinnamic Acid Derivatives as Matrices for Ultraviolet Laser Desorption Mass Spectrometry of Proteins. Rapid Communication in Mass Spectrometry (1989), Vol. 3, No. 12, pages 432-435 describe the use of hydroxy or methoxy-substituted cinnamic acids as matrices in MALDI mass spectrometry. The corresponding use of α-cyanocinnamic acid can be derived from US 2002/0142982 A1. DE 101 58 860 A1 and DE 103 22 701 A1 describe the use of α-cyano-4-hydroxy cinnamic acid or 3,5-dimethoxy-4-hydroxy cinnamic acid. Finally, US 2006/0040334 A1 and WO 2006/124003 A1 disclose MALDI matrices on the basis of analyte-coupled or polymer-coupled derivatives of α-cyano-4-hydroxy cinnamic acid.

The matrices which can be used for MALDI mass spectrometry must satisfy a large number of requirements simultaneously. First of all, they must be capable of inserting analytes (by co-crystallisation) into the matrix crystal and isolating them from other analytes. In addition, they need to be soluble in solvents which are compatible with the analyte, stable under vacuum and capable of absorbing the laser wavelength of the laser used. Furthermore, they should cause the co-desorption of the matrix and analyte under laser irradiation and promote analyte ionisation.

For the matrix compounds used so far, the characteristics and hence the performance data of MALDI mass spectrometry are still capable of improvement, especially with regard to their detection and sensitivity for positive ions, negative ions and ions with a double charge and higher.

It is therefore a problem of the present invention to provide compounds which can be used as matrices in MALDI mass spectrometry and which at least partially overcome the disadvantages known from the state of the art. In particular, a problem is to improve the detection and sensitivity for positive ions, negative ions and ions with a double charge and higher.

This problem is solved by the use of cyanocinnamic acid derivatives of the general formula:

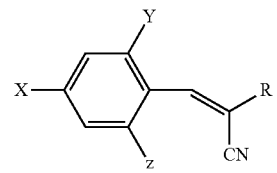

where X is selected from Cl, F, Br, I and substituted and unsubstituted $C_1$-$C_{10}$ alkyl; Y and Z are independently selected from H, Cl, F, Br, I and substituted and unsubstituted $C_1$-$C_{10}$ alkyl; and R is selected from COOH, $CONH_2$, $SO_3H$ and COOR' with R'=$C_1$-$C_{10}$ alkyl as the matrix for the MALDI mass spectrometry of an analyte. The structural formula shown is intended to include all possible cis/trans isomers of the cyanocinnamic acid derivatives.

It is preferable that X is selected from F, Cl, methyl or $C_2$-$C_{10}$ alkyl and Y and Z are independently selected from H, F and Cl.

It is also proposed that the cyanocinnamic acid derivative is 2,4-difluoro-cyanocinnamic acid, 4-chloro-cyanocinnamic acid or 4-methyl cyanocinnamic acid.

In a preferred embodiment, 4-chloro-cyanocinnamic acid is the matrix for the MALDI mass spectrometry of positive ions.

In a further preferred embodiment, 2,4-difluoro-cyanocinnamic acid, 4-chloro-cyanocinnamic acid and 4-methyl-cyanocinnamic acid are matrices for the MALDI mass spectrometry of negative ions.

In addition, it is proposed that 2,4-difluoro-cyanocinnamic acid is the matrix for the MALDI mass spectrometry of negative and positive ions.

In yet a further preferred embodiment, 4-methyl-cyanocinnamic acid and 4-chloro-cyanocinnamic acid are matrices for the MALDI mass spectrometry of doubly charged ions.

It is also preferred that the analyte is a digested protein or peptide. Nevertheless, undigested proteins, polynucleic acids, saccharides and the like are also conceivable as analytes.

It is also preferred that the matrix is mixed with the analytes.

In addition, it is proposed that the molar mixing ratio of analyte to matrix should be 1:1,000 to 1:1,000,000,000, preferably 1:100,000-1:10,000,000.

It is also preferably proposed that mixtures of different cyanocinnamic acid derivatives falling under the above general formula or a mixture of at least one cyanocinnamic acid derivative falling under the above general formula are/is used with an additional matrix.

Finally, it is proposed that the additional matrix is selected from α-cyano-4-hydroxy cinnamic acid, 2,5-dihydroxy benzoic acid or sinapic or ferulic acid.

Similarly, 2-aza-5-thiothymine or 3-hydroxy picolinic acid may be used as an additional matrix.

It is equally conceivable that the matrix materials used are mixed with an inert filler.

It has surprisingly been found in accordance with the invention that when the cyanocinnamic acid derivatives listed above are used as the matrix in MALDI mass spectrometry, the detection and sensitivity for positive ions, negative ions and ions with a double charge and higher can be improved substantially.

In particular, a distinct improvement in the sensitivity of biological polymer analytes, preferably peptide analytes, was achieved. Furthermore, the use in accordance with the invention exhibits low selectivity for peptides of various amino acid compositions and hence substantially lower discrimination effects in the MALDI mass spectra than with the matrices used so far, as a result of which more species of analyte can be detected in an analyte mixture than has been the case hitherto. The use of matrix mixtures of the cyanocinnamic acid derivatives described above makes it possible to optimise the characteristics with regard to crystallisation and the insertion of analyte compounds into the matrix crystals and more efficient ionisation of the analytes. It has likewise surprisingly been found that cyanocinnamic acid derivatives with substituents with similar electronic properties, such as $NO_2$, CN or acetyl, do not achieve results anywhere near as good as the cyanocinnamic acid derivatives used in accordance with the invention.

Figure 6:
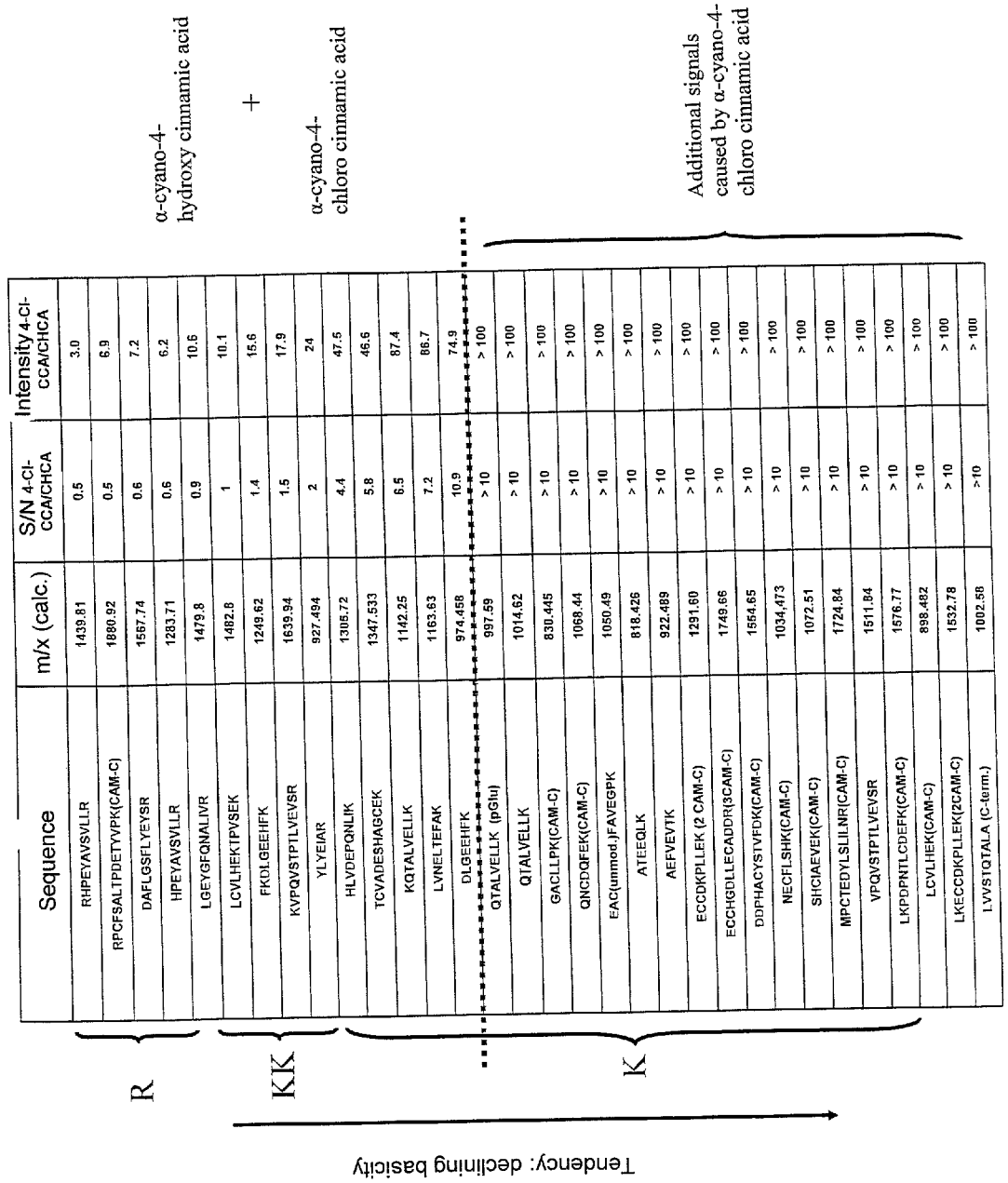
Figure 7:
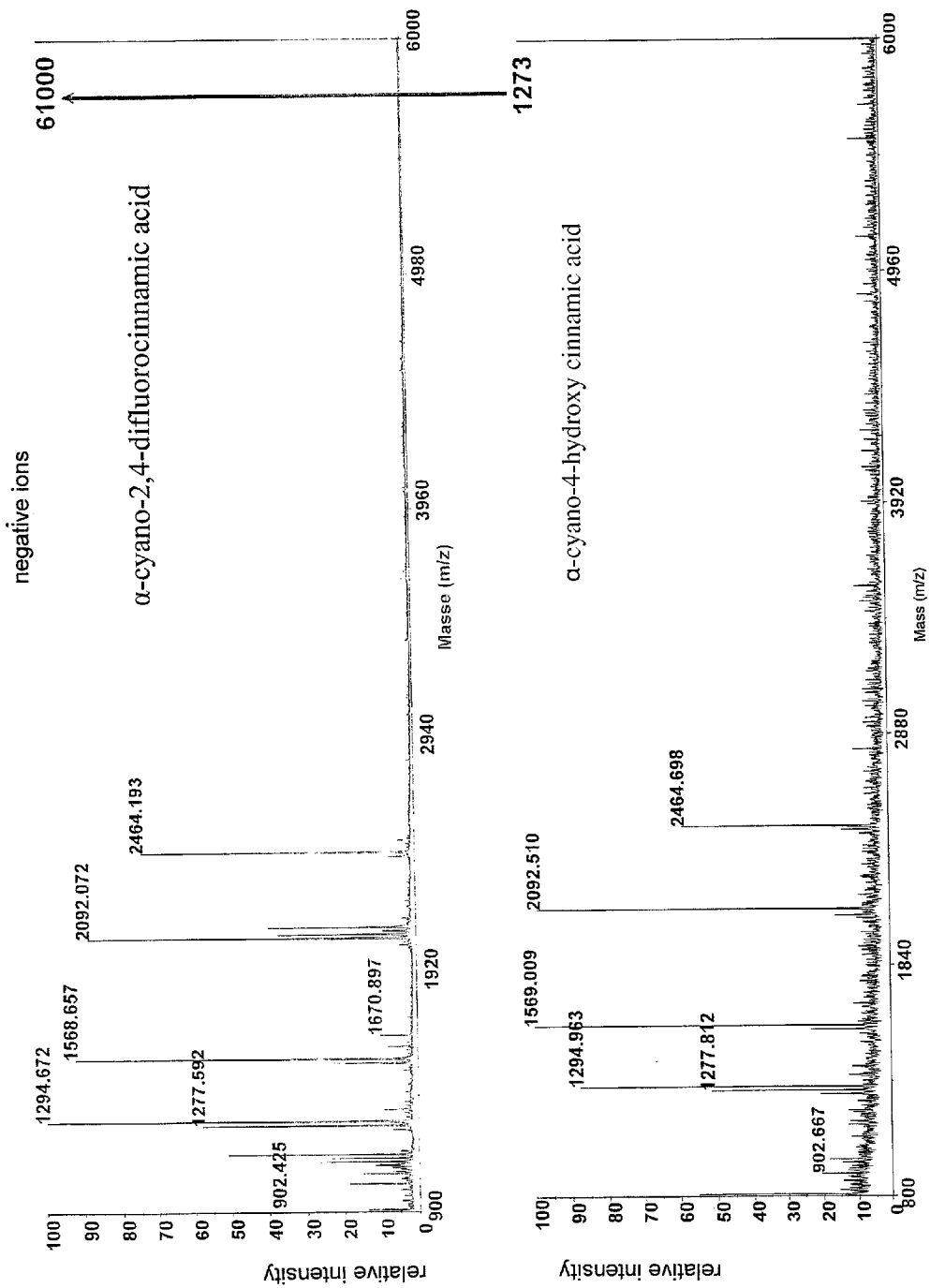
Figure 8:
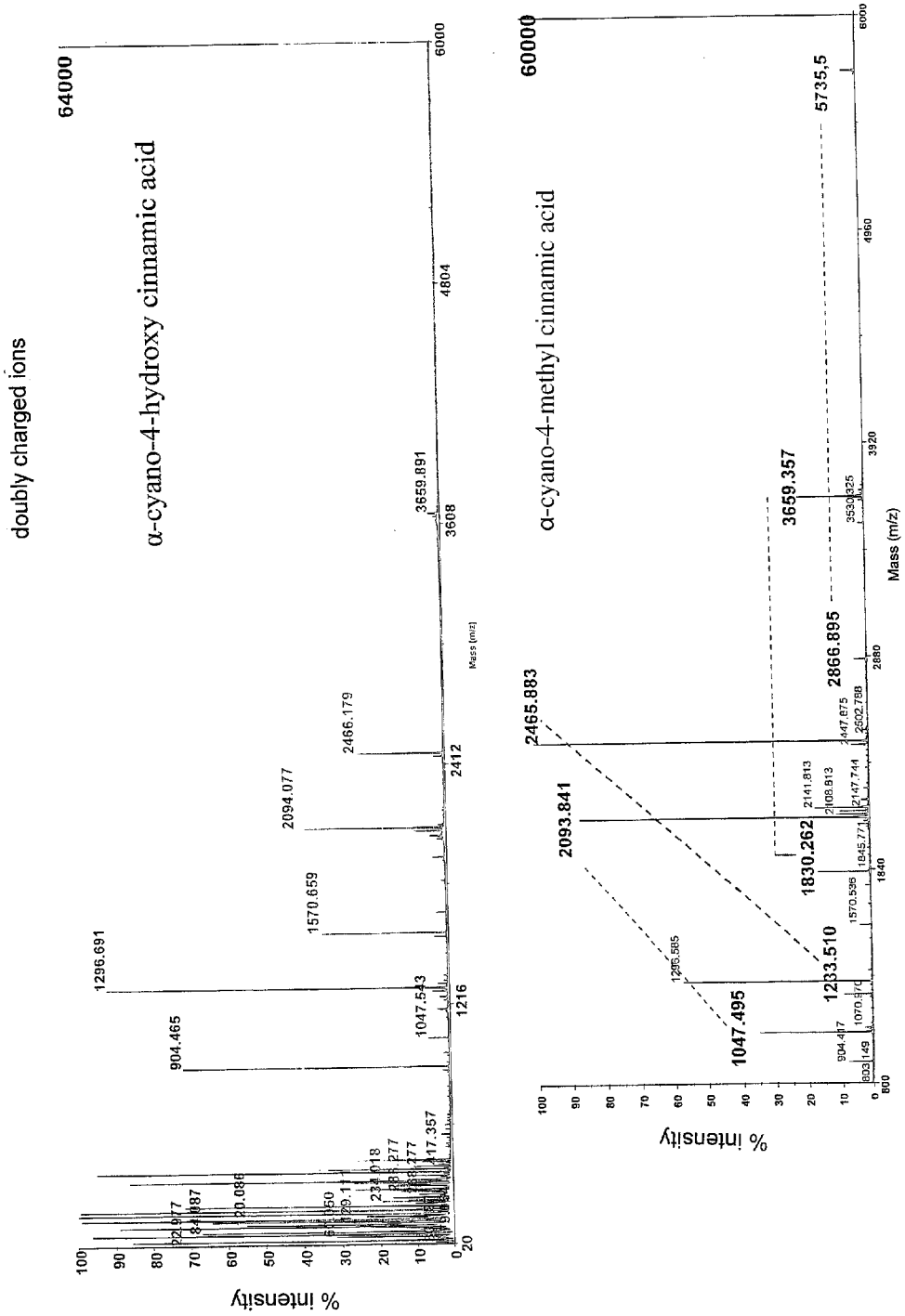

Further features and advantages of the invention will become clear from the following detailed description of preferred embodiments in combination with the attached drawings, in which FIGS. 1-5 show excerpts from mass spectra of BSA protein digestion (BSA: bovine serum albumin), in a comparison using the α-cyano-4-hydroxy cinnamic acid employed so far and the newly used α-cyano-4-chloro cinnamic acid as the matrix;

FIG. 6 lists in the form of a table all the detectable peptides of BSA protein digestion;

FIG. 7 shows a comparison of mass spectra for negative ions of α-cyano-4-hydroxy cinnamic acid and α-cyano-2,4-difluoro cinnamic acid as the matrix; and FIG. 8 shows mass spectra for doubly charged ions using α-cyano-4-hydroxy cinnamic acid and α-cyano-4-methyl cinnamic acid.

Cyanocinnamic acid derivatives which may be used in accordance with the invention can be prepared, for example, by condensation of the corresponding aldehyde with cyanoacetic acid (derivatives) according to a Knoevenagel condensation.

EXAMPLE 1

2 g cyanoacetic acid (1 eq., 23.5 mmol), 2.97 g chlorobenzaldehyde (0.9 eq., 21.1 mmol) and 300 mg ammonium acetate (15% (m/m) based on the acid) are heated in 30 ml toluene using a water separator with reflux. After completion of the water separation (about 3 hours), the mixture is cooled to room temperature, in the course of which the product usually precipitates in crystalline form. After filtration, the crude product is washed with sufficient water. If no product precipitates, the mixture is concentrated and the remaining solids are washed with sufficient water. The crude product is repeatedly recrystallised from a mixture of alcohol (methanol) and water. Further purification takes place by means of ion exchange (strong cation exchanger), with 50% acetonitrile being used as the solvent. The eluate is concentrated at room temperature, in the course of which the purified product precipitates in crystalline form. After filtering and drying in a vacuum, 3.35 g (78% of the theoretical yield) α-cyano-4-chloro cinnamic acid are obtained.

EXAMPLE 2

1.25 times the amount of cyanoacetic acid, based on the amount of aldehyde, is dissolved in a beaker together with 1.1 times the amount of soda, based on the amount of cyanoacetic acid, at 30° C. in 40 ml water. The solution is transferred to a flask, and the subsequent reaction takes place at about 30° C. Sodium hydroxide (0.125 times the amount based on the amount of cyanoacetic acid) dissolved in 15 ml water is added to the solution. The aldehyde—if it is not liquid—is dissolved in the smallest possible volume of acetonitrile and added gradually over a period of about 30 minutes, accompanied by vigorous stirring. After stirring for 2 hours, the solution is transferred to a beaker and acidified with concentrated hydrochloric acid; the solution is cooled in an ice bath and suction-filtered. The precipitate is washed with a little cold water and toluene (if insoluble) and dried under a vacuum at 40° C. Purification is performed as in Example 1. The yields are about 50-70% of the theoretical amounts.

The cyanocinnamic acid derivatives can be mixed with the analytes using standard procedures, in order to prepare a suitable sample for MALDI mass spectrometry.

One exemplary method of mixing is the dried droplet method. In this process, the matrix and analyte are dissolved and applied simultaneously (by premixing) or consecutively to any surface. Evaporation of the solvent causes crystallisation of the matrix including the analyte compounds.

The surface preparation method may also be used, in which the matrix or the matrix mixture is dissolved and applied to any surface without the analyte. Evaporation of the solvent causes (co-) crystallisation of the matrix compound(s). The dissolved analyte is applied to the crystalline matrix, in the course of which dissolution only of matrix layers close to the surface leads to the inclusion of the analyte compound in concentrated form upon recrystallisation.

The sublimation method corresponds to the surface preparation method except that the matrix is not crystallised out of a solution, but is applied to a surface by deposition from the gas phase with sublimation.

Finally, an "airbrush method" is possible, in which the matrix and the analyte are dissolved in a common solvent (mixture) and distributed dispersedly by means of a spray apparatus (aerosol formation). The large surface area causes rapid evaporation of the solvent, accompanied by the formation of matrix/analyte crystals. Alternatively, the matrix may also be dissolved without the analyte and applied to surfaces to be investigated (such as portions of fabric) by spraying or other means.

A novel field of application is the preparation of the matrix as an ionic liquid: for this purpose, the dissolved matrix is mixed with an equimolar amount of cationisable base, such as pyridine or diethylamine, and rotated in, as a result of which a liquid ionic matrix film forms, which can be applied to any surfaces with the analyte solution.

In the following, "digestion" is used to mean a protein cleaved enzymatically in specific amino acid positions, giving rise to a large number of smaller peptides.

A Voyager-DE STR mass spectrometer ex Applied Biosystems was used for the experiments performed.

The mass spectrometer separates different species of ions (analyte ions, matrix ions) according to their mass-to-charge ratio. Normally, the ions in MALDI only carry one (positive or negative) charge, so that when charge=1, the mass-to-charge ratio is equal to the mass of the ions. The abscissa of the spectra shows the mass-to-charge ratio (and thus in almost all cases the mass) of the ions, the unit being Daltons or g/mol.

Stronger signals—which are indicated by vertical lines, the length of the lines (signals) correlating with the amount of ion species causing that signal—are labelled individually with their mass or mass-to-charge ratio.

The ordinate scale depends on the strongest signal within the spectrum concerned and indicates the absolute value of the strongest signal, which depends on the equipment used. All the other signals shown in the spectrum are drawn relative to the strongest signal (left-hand ordinate axis). The right-hand ordinate value is only meaningful for comparisons with further signals within a spectrum or other spectra of the same mass spectrometer. For example, the numerical values at the top right in FIGS. 1-5 "BSA digestion—1 fmol effectively applied" indicate the absolute intensities of the strongest signal in each case (with the mass 689.378 in the upper spectrum when using the new matrix α-cyano-4-chloro cinnamic acid in FIG. 1). The peptide with the mass m/z=927.495 has a relative intensity of 88% (which can be read from the left-hand ordinate scale) compared to the intensity of the strongest ion at m/z=689.378 and thus an intensity 6,152 abs. units. In the lower CHCA spectrum of the known matrix α-cyano-4-hydroxy cinnamic acid, the same signal at m/z=927.494 only has an absolute intensity of 253.1 units (calculated according to the strongest signal at m/z=675.635 with 627.0 units, where the BSA peptide signal at m/z=927.494 has a relative intensity of 40.37%). With this exemplary ion, the novel matrix thus makes it possible for the absolute intensity to increase by a factor of about 25, which means that this peptide in combination with the novel matrix forms considerably more ions and thus causes noticeably stronger signals, which are easier to measure. The advantage is that weak signals, which could not be detected hitherto, can now be measured because of the amplification, which can be seen, for example, in FIG. 2, BSA digestion—1 fmol effectively applied (950-1,100): The novel matrix (upper spectrum) makes it possible to detect analytes which could not be detected with the older matrix (the best so far—lower spectrum). For a more precise classification, the amino acid compositions of the peptides causing the signal concerned were also added to most signals, the amino acid modification corresponding to the regular 1-letter code. Possible peptide modifications are shown in subsequent brackets (CAM-C: carbamido methylation of cysteine, pGlu: pyroglutamine modification, C-term.: C-terminal fragment). The weaker signals following the signals, with a mass increase of 1 Da are due to the $^{13}C$ isotopes of the peptides concerned. The improved results can be seen from all the FIGS. 1-5.

FIG. 6 lists all the detectable peptides of the BSA-protein digestion used. The amount of the detectable peptides depends on the amount of protein originally used, which in this case was 1 fmol, which is a very small amount. The upper half shows the peptides which are detectable with the CHCA matrix used so far (synonym HCCA or α-cyano-4-hydroxy cinnamic acid). The lower half lists all those peptides which, in addition to the upper half, are only detectable with the novel matrix. It is immediately apparent from this that an immense gain in information is provided. The first column lists the amino acid sequences of the peptides concerned, while the second column shows their mass. In this column, the S/N (signal to noise)—ratio is shown, which indicates the intensity and detectability of a signal: for a variety of reasons, the entire spectrum includes a slight noise, which always occurs, even when no analytes are contained. In order to be detected, signals must have higher intensities than the noise; otherwise, they are not detectable. The S/N ratio is calculated by a computer and indicates how many times stronger a signal is relative to the background noise. This means: the higher it is, the easier the signal is to recognise and detect. In the third column, the S/N ratio of the novel matrix relative to the old matrix has been included, values>1 thus indicate that these signals are stronger and hence easier to detect. In the fourth column, the ratio of the absolute intensities is shown, and again the principle is that the bigger they are, the easier a signal is to recognise as such; it can clearly be seen that the novel matrix produces considerably stronger signals than the old matrix.

The results discussed for FIGS. 1-5, which represent a considerable improvement over the state of the art, can also be seen in the mass spectra of FIGS. 7 and 8 for negative and doubly charged ions respectively.

The features of the invention disclosed in the above description, in the claims and in the drawings can be essential to implementing the invention in its most varied embodiments both individually and in combination.

The invention claimed is:
1. A method of improving the detection and sensitivity in MALDI mass spectrometry, comprising:
preparing a matrix for MALDI mass spectrometry comprising α-cyanocinnamic acid derivatives of the general formula

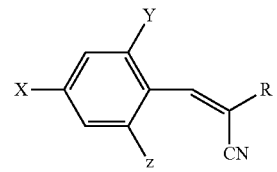

where either:
1) X is selected from Cl, F, Br, and I, and Y and Z are hydrogen; or
where X and Y are independently selected from Cl, F, Br, and I, and Z is selected from H, Cl, F, Br, and I; or
where X and Z are independently selected from Cl, F, Br, and I, and Y is selected from H, Cl, F, Br, and I; or
2) X is a substituted or unsubstituted $C_1$-$C_{10}$ alkyl, and Y and Z are hydrogen; or
where X and Z are independently selected from unsubstituted $C_1$-$C_{10}$ alkyls, and Y is hydrogen; or
where X, Y and Z are independently selected from unsubstituted $C_1$-$C_{10}$ alkyls; and
3) R is selected from COOH, $CONH_2$, $SO_3H$ and COOR' with R'=$C_1$-$C_{10}$ alkyl;
mixing the matrix with an analyte; and
performing MALDI mass spectrometry of the mixture.
2. The method of claim 1, wherein X is selected from F, Cl and Br, and Y is selected from H, F, Cl, and Br, and Z is selected from H, F, Cl and Br; or wherein X is methyl and Y and Z are independently selected from H and methyl.

3. The method of claim 1, wherein the α-cyanocinnamic acid derivative is 2,4-difluoro-α-cyanocinnamic acid, 4-chloro-α-cyanocinnamic acid or 4-methyl-α-cyanocinnamic acid.

4. The method of claim 1, wherein 4-chloro-α-cyanocinnamic acid is the matrix for the MALDI mass spectrometry of positive ions.

5. The method of claim 1, wherein 2,4-difluoro-α-cyanocinnamic acid, 4-chloro-α-cyanocinnamic acid and 4-methyl-α-cyanocinnamic acid are matrices for the MALDI mass spectrometry of negative ions.

6. The method of claim 1, wherein 2,4-difluoro-α-cyanocinnamic acid is the matrix for the MALDI mass spectrometry of negative and positive ions.

7. The method of claim 1, wherein 4-methyl-α-cyanocinnamic acid and 4-chloro-α-cyanocinnamic acid are matrices for the MALDI mass spectrometry of ions with a double charge or higher.

8. The method of claim 1, wherein the analyte is a digested protein or peptide.

9. The method of claim 1, wherein mixtures of different α-cyanocinnamic acid derivatives according to claim 1 or a mixture of at least one α-cyanocinnamic acid derivative according to claim 1 is used with an additional matrix.

10. The method of claim 9, wherein the additional matrix is selected from α-cyano-4-hydroxy cinnamic acid, 2,5-dihydroxy benzoic acid or sinapic or ferulic acid.

* * * * *